US005789204A

United States Patent [19]

Kogtev et al.

[11] Patent Number: 5,789,204
[45] Date of Patent: Aug. 4, 1998

[54] BIOSORBENT FOR HEAVY METALS PREPARED FROM BIOMASS

[75] Inventors: Leonid Semionovich Kogtev, Moscow, Russian Federation; Jin Kyu Park; Jin Kyuk Pyo, both of Seoul, Rep. of Korea; Young Keun Mo, Chungbook, Rep. of Korea

[73] Assignee: Dong Kook Pharmaceutical Co., Ltd., Seoul, Rep. of Korea

[21] Appl. No.: 585,823

[22] Filed: Jan. 16, 1996

[30] Foreign Application Priority Data

Oct. 20, 1995 [KR] Rep. of Korea ............ 95-36304

[51] Int. Cl.$^6$ ............ C12P 19/00; C12P 19/26; C12P 19/28
[52] U.S. Cl. ............ 435/85; 435/72; 435/84
[58] Field of Search ............ 435/72, 84, 85

[56] References Cited

FOREIGN PATENT DOCUMENTS

1693055 A1  11/1991  U.S.S.R.

OTHER PUBLICATIONS

European J. Appl. Microbiol. Biotechnol (1981) 12:76–83; Akira Nakajima et al.: Studies on the Accumulation of Heavy Metal Elements in Biological Systems.

Applied Microbiology and Biotechnology (1992), 37:399–403; Eric Fourest et al.: Heavy metal biosorption by fungal mycelial by-products: mechanisms and influence of pH.

European J. Appl. Microbiol. Biotechnol (1982) 16:88–91; Akira Nakajima et al.: Recovery of Uranium by Immobilized Microorganisms.

Biotechnology and Bioengineering, vol. XXIII, (1981) pp. 583–604; Marios Tsezos et al.: Biosorption of Uranium and Thorium.

Biotechnology and Bioengineering, vol. XXIV, (1982) pp. 385–401, M. Tsezos et al.: The Mechanism of Uranium Biosorption by *Rhizopus arrhizus*.

Applied Microbiology and Biotechnology (1991) 34:688–692; Edith Luef et al.: Biosorption of zinc by fungal mycelial wastes.

*Journal of Industrial Microbiology,* (1994), 13:126–130; J.M. Tobin et al.: Metal accumulation by fungi: applications in environmental biotechnology.

Biotechnology and Bioengineering, vol. 32 (1988) pp. 545–553; M. Tsezos et al.: A Batch Reactor Mass Transfer Kinetic Model for Immobilized Biomass Biosorption.

Applied and Environmental Microbiology (1981), pp. 237–245, Gerald W. Strandberg et al.: Microbial Cells as Biosorbents for Heavy Metals: kAccumulation of Uranium by *Saccharomyces cerevisiae* and *Pseudomonas aeruginosa*.

*Primary Examiner*—John W. Rollins
*Assistant Examiner*—Christopher R. Tate
*Attorney, Agent, or Firm*—Kenyon & Kenyon

[57] ABSTRACT

The object of this invention is to provide a biosorbent for heavy metals having polyaminosaccharide sodiumphosphate as main ingredient prepared from microbial biomass using *Aspergillus, Penicillium, Trichoderma* or *Micrococcus* genus originating from industrial fermentations and biological treatment plants.

5 Claims, 1 Drawing Sheet

BIOSORBENT FOR HEAVY METALS PREPARED FROM BIOMASS

BACKGROUND OF THE INVENTION

1. Field of the Invention

This invention relates to a biosorbent for heavy metals prepared from waste microbial biomass originating from industrial fermentations and biological treatment plants, and a method of recovering heavy metals using this biosorbent.

2. Description of Prior Art

Accumulation of metals by microorganisms has been known for a few decades but has received more attention in recent years, because of its potential application in environmental protection or recovery of precious or strategic metals. The general term 'biosorption' has been used to describe a property of microbial biomass to retain ions of mainly heavy metals and radionuclides. Increased interest in sequestering these elements by nonliving microbial biomass has been based on potential technological applications of biosorption in metal recovery and industrial wastewater treatment.

Filamentous fungi have been used in fermentation industries to produce various metabolites such as enzymes, flavourings or antibiotics. Thousands of tons of residual biomass produced each year contain poorly biodegradable biopolymers (cellulose, chitin, glucans, etc.) and make bad fertilizers for agricultural use. To date, incineration is the main way of destroying this by-product. On the other hand, mining, metallurgy industries or galvanizing plants produce highly metal-loaded waste water. Existing treatments to purify these effluents are often less affordable than the taxes required to dispose of them in effluent. Thus, with continued extraction of mineral resources and environmental accumulation of hazardous waste, greater efficiency in detoxification of effluents and recovery of metals must be devised.

Some kinds of microorgnisms, such as, *Saccharomyces cerevisiae, Actinomyces levoris, Pseudomonas aeruginosa, Streptomyces viridochromogenes* and *Rhizopus arrhizus* have been reported to have biosorption property for accumulating heavy metal ions. The following are the conventional biosorbents for heavy metals and radionuclides disclosed in papers.

Gerald Strandberg et al. reported that uranium accumulated extracellularly on the surfaces of *Saccharomyces cerevisiae* cells, and that the rate and extent of accumulation were subject to environmental parameters, such as, pH, temperature, and interference by certain anions and cations (*Applied and Enviornmental Microbiology*, Vol 41, 1981, pp237–245).

Mario Tsezos et al. reported that the biomass of *Rhizopus arrhizus* at pH 4 exhibited the highest uranium and thorium biosorptive uptake capacity (*Biotechnology and Bioengineering*, Vol XXIII, 1981, pp583–604).

Akira Nakajima et al. reported that immobilized *Streptomyces viridochromogenes* in polyacrylamide gel have the most favorable features for uranium recovery from sea and water (*Eur. J. Applied microbiology and Biotechnology*, Vol 16, 1982, pp88–91).

SUMMARY OF THE INVENTION

The object of this invention is to provide a biosorbent for heavy metals having polyaminosaccharide sodiumphosphate as main ingredient prepared from microbial biomass using *Aspergillus, Penicillium, Trichoderma* or *Micrococcus* genus originating from industrial fermentations and biological treatment plants.

And, the further object of this invention is to provide a method for preparing above biosorbent with following steps. A method for preparing above biosorbent comprises i) hydrolysis of biomass with phosphoric acid solution, ii) removal of lipid soluble materials with butanol or n-hexane, iii) reaction and alkalization with sodium hydroxide or sodium bicarbonate solution to, iv) removal of soluble materials with lower alcohols, and v) filtering and drying the remaining residue to obtain the biosorbent for heavy metals having polyaminosaccharide sodium phosphate as main ingredient.

DETAILED DESCRIPTION OF THE INVENTION

Figure 1:
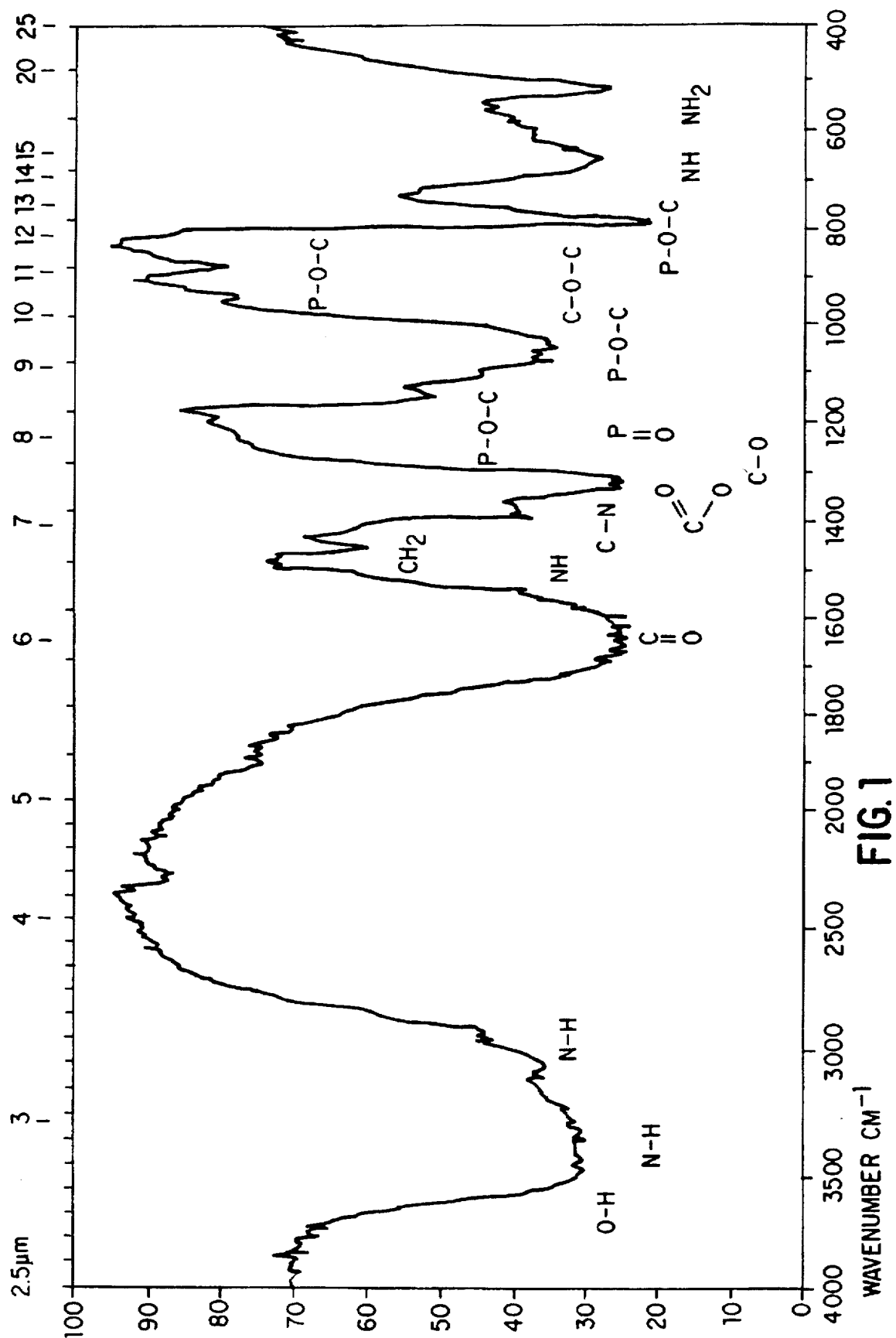
FIG. 1 shows the IR specturm of biosorbent prepared by present invention.

The mechanism how polyaminosaccharide sodium phosphate can be used as biosorbent for heavy metals is explained as follows.

The mechanism of biosorption has been thought to be involved in adsorption, ion exchange, co-ordination and covalent bonding. As a result of various experiments, the specific ingredients in cell wall of microorganism have been thought to be involved in biosorption. Furthermore, the chitin and glucan complex in microbial biomass has been known to make a key role for biosorption. However, chitin and chitosan in crab shell show less biosorption property than that made from microbial biomass. In addition, mureine in cell wall of microorganism has been known to contribute to the formation of metal ion complex. Considering all ingredients of cell wall in fungi and bacteria, polyaminosaccharides are the optimal biosorbent having best biosorption property.

Therefore, the present invention relates to a method for easily extracting polyaminosaccharide ingredients from microbial biomass. The microbial biomass using *Aspergillus, Penicillium, Trichoderma* or *Micrococcus* genus from industrial fermentations or biological treatment plants is used as raw material of this invention.

A process for preparing biosorbent of this invention can be explained as follows.

The microbial biomass using *Aspergillus niger, Penicillium chrysogenum, Trichoderma reesei* or *Micrococcus luteus* from industrial fermentations or biological treatment plants is placed in the reactor. The biomass is hydrolyzed with 0.5~5.0% of phosphoric acid aqueous solution at 20°~60° C. for 2~5 hours. The residue after hydrolysis is washed with distilled water and the soluble materials are removed. The lipid soluble organic solvent, such as, butanol or n-hexane is added and the lipid soluble materials are removed. After removing organic solvent, the aqueous solution of 1~40% sodium hydroxide or sodium bicarbonate is added and reacted to alkalify the residue at 20°~100° C. for 1~10 hours. On the condition of pH 9~12, the lower alcohol, such as, methanol, ethanol, isopropanol or mixture of them is added and lower alcohol soluble materials are removed. Finally, the remaining residue is filtered and dried to obtain the biosorbent having polyaminosaccharide sodiumphosphate as main ingredient.

The most important preparation step for preparing biosorbent of this invention is to react the residue with NaOH or $NaHCO_3$ solution. In this step, the phosphate ions($PO_4^{-3}$) of polyaminosaccharide in microbial biomass are converted into sodium phosphate. These converted sodium phosphates contribute to the biosorption of heavy metals in combination with amine radicals in polymer to form the binding sites for heavy metals.

Therefore, the biosorbent of this invention is the polymer of following aminosaccharide sodium phosphate, and the number average molecular weight of this biosorbent is 50,000~200,000.

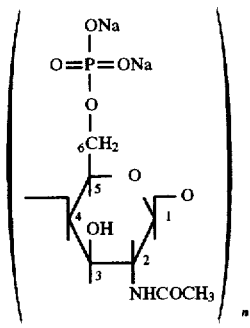

Followings are analytical data of the biosorbent of this invention.

FIG. 1 shows the IR specturm of biosorbent prepared by present invention. Absorption wave lengths (cm$^{-1}$) are 3000~3500, 2300, 1650, 1550, 1470, 1380, 1320~1340, 1160, 1050, 900, 780, 600. The contents of polyaminosaccharide sodium phosphate in biosorbent are 50~80(w/w) % of total biosorbent compositions.

1 gram of dried biosorbent contains 200~400 mg of glucosamine, 60~200 mg of glucose, 70~200 mg of amino acid, 30~50 mg of organic phosphorous compounds and other residual compounds.

The biosorbent prepared by above process having polyaminosaccharide sodium phosphate as main ingredient can be used for recovery of heavy metals from waste streams. Therefore, this biosorbent can be applied to the columns for purifying the waste streams or to the reactors for purifying waste streams.

This invention can be explained in detail by following examples. However, these examples do not limit the scope of this invention.

The biosorption property for heavy metals was measured by following method. 200 mg of dried biosorbent was added to 20 ml of standard metal nitrate solution containing 5 mg of metal ions per 1 ml water. In room temperature, the mixture was stirred for 1 hour, and the solution was filtered and separated. After 100 times dilution of filtered solution, the quantity of metals was measured by atomic absorption analyzer.

(EXAMPLE 1)
Preparation of biosorbent from microbial biomass using Aspergillus niger 1 L of 1% phosphoric acid solution was added to 200 g of well-dried microbial biomass using Aspergillus niger ATCC-9642 and the biomass was hydrolyzed for 3 hours in room temperature. After washing with distilled water, 500 ml of butanol was added to residue. The lipid soluble materials were removed. After removal of butanol, 10% NaOH solution was added and reacted at 50° C. for 3~5 hours. On pH 10~12, 600 ml of ethanol was added to remove the ethanol soluble materials. Finally, remaining residue was filtered and dried at 100~130° C. Finally, dried biosorbent was crushed to obtain the 0.5~2.0 mm particle size. Table 1 showed the analytical data of biosorbent. Yield was 48% and obtained biosorbent had following biosorption property.

| Metal | Metal Biosorption (mg/g) |
| --- | --- |
| Cu | 250 |
| Pb | 100 |
| Cd | 126 |
| Zn | 80 |
| Hg | 150 |
| Ni | 145 |
| Co | 100 |
| Cs | 30 |
| Sr | 40 |
| U | 210 |
| Pu | 210 |
| Er | 250 |
| Am | 320 |
| Ag | 55 |
| Au | 35 |

(EXAMPLE 2)
Preparation of biosorbent from microbial biomass using Penicillium chrysogenum 800 ml of 1.5% phosphoric acid solution was added to 200 g of wet microbial biomass using Penicillium chrysogenum ATCC-10003 and the biomass was hydrolyzed for 2 hours in room temperature. After washing with distilled water, 600 ml of hexane was added to residue. The lipid soluble materials were removed. After removal of hexane, 20% NaHCO$_3$ solution was added and reacted at 90° C. for 2 hours. On pH 10~12, 500 ml of ethanol was added to remove the ethanol soluble materials. Finally, remaining residue was filtered and dried at 100~130° C. Finally, dried biosorbent was crushed to obtain the 0.5~2.0 mm particle size. Table 1 showed the analytical data of biosorbent. Yield was 40% and obtained biosorbent had following biosorption property.

| Metal | Metal Biosorption (mg/g) |
| --- | --- |
| Cu | 280 |
| Pb | 100 |
| Cd | 120 |
| Zn | 80 |
| Hg | 180 |
| Ni | 150 |
| Co | 120 |
| Cs | 20 |
| Sr | 60 |
| U | 250 |
| Pu | 300 |
| Er | 280 |
| Am | 300 |
| Ag | 50 |
| Au | 40 |

(EXAMPLE 3)
Preparation of biosorbent from microbial biomass using Trichoderma reesei 500 ml of 1.5% phosphoric acid solution was added to 100 g of wet microbial biomass using Trichoderma reesei ATCC-26921 and the biomass was hydrolyzed for 3 hours in room temperature. After washing with distilled water, 300 ml of butanol was added to residue. The lipid soluble materials were removed. After removal of butanol, 10% NaOH solution was added and reacted at 100° C. for 1 hours. On pH 10~12, 300 ml of ethanol was added to remove the ethanol soluble materials. Finally, remaining residue was filtered and dried at 100~130. Finally, dried biosorbent was crushed to obtain the 0.5~2.0 mm particle size. Table 1 showed the analytical data of biosorbent. Yield was 38% and obtained biosorbent had following biosorption property.

| Metal | Metal Biosorption (mg/g) |
|---|---|
| Cu | 90 |
| Pb | 120 |
| Cd | 65 |
| Zn | 80 |
| Hg | 100 |
| Ni | 120 |
| Co | 95 |
| Cs | 20 |
| Sr | 35 |
| U | 235 |
| Pu | 150 |
| Er | 180 |
| Am | 245 |
| Ag | 35 |
| Au | 20 |

(EXAMPLE 4)

Preparation of biosorbent from microbial biomass using *Micrococcus luteus*

800 ml of 2.0% ortho phosphoric acid solution was added to 200 g of well-dried microbial biomass using *Micrococcus luteus* ATCC-4698 and the biomass was hydrolyzed for 3 hours in room temperature. After washing with distilled water, 500 ml of butanol was added to residue. The lipid soluble materials were removed. After removal of butanol, 10% NaOH solution was added and reacted at 40° C. for 3~5 hours. On pH 10~12, 400 ml of methanol was added to remove the methanol soluble materials. Finally, remaining residue was filtered and dried at 100~130° C. Finally, dried biosorbent was crushed to obtain the 0.5~2.0 mm particle size. Table 1 showed the analytical data of biosorbent. Yield was 45% and obtained biosorbent had following biosorption property.

| Metal | Metal Biosorption (mg/g) |
|---|---|
| Cu | 240 |
| Pb | 90 |
| Cd | 106 |
| Zn | 90 |
| Hg | 140 |
| Ni | 130 |
| Co | 90 |
| Cs | 30 |
| Sr | 40 |
| U | 200 |
| Pu | 220 |
| Er | 240 |
| Am | 300 |
| Ag | 50 |
| Au | 35 |

TABLE 1

Analytical data of biosorbents

| No. of Example | % of PAS* | Molecular Weight | Glucosamine mg/g** | Glucose mg/g** | Amino acids mg/g** | Phospho comps. mg/g** | Residual lipids mg/g** |
|---|---|---|---|---|---|---|---|
| 1 | 66 | 120,000~180,000 | 320 | 112 | 120 | 42.4 | 8 |
| 2 | 74 | 100,000~150,000 | 380 | 68 | 80 | 37.5 | 12 |
| 3 | 57 | 80,000~120,000 | 310 | 230 | 70 | 36.8 | 15 |
| 4 | 61 | 50,000~80,000 | 195 | 45 | 210 | 48.3 | 5 |

* PAS: polyaminosaccharide sodiumphosphate
** 1 gram of dried biosorbent (EXAMPLE 5)

Biosorption for heavy metals from waste sludge

Using the biosorbent prepared in example 1, the heavy metals were recovered from waste sludge stream. The amount of biosorbent input to sludge stream was 1% of sludge by weight. Table 2 showed the quantity of heavy metals before and after treatment of biosorbent.

(EXAMPLE 6)

Biosorption for heavy metals from waste sludge

Using the biosorbent prepared in example 2, the heavy metals were recovered from waste sludge stream. The amount of biosorbent input to sludge stream was 1% of sludge by weight. Table 2 showed the quantity of heavy metals before and after treatment of biosorbent.

(EXAMPLE 7)

Biosorption for heavy metals from waste sludge

Using the biosorbent prepared in example 3, the heavy metals were recovered from waste sludge stream. The amount of biosorbent input to sludge stream was 1% of sludge by weight. Table 2 showed the quantity of heavy metals before and after treatment of biosorbent.

TABLE 2

The quantity of heavy metal ions before and after treatment of biosorbent

| No. of Example | Metal | Quantity of heavy metals | | |
|---|---|---|---|---|
| | | Before (mg/l) | After (mg/l) | Biosorption (%) |
| 5 | Fe | 0.5 | 0.02 | 96 |
| | Cu | 2.2 | 0.4 | 82 |
| | Ni | 3.7 | 1.3 | 65 |
| | Cd | 0.1 | 0.04 | 60 |
| | Pb | 1.5 | 0.4 | 74 |
| | Ag | 0.05 | 0.01 | 80 |
| 6 | Fe | 9.2 | 2.3 | 75 |
| | Cu | 2.4 | 0.7 | 71 |
| | Ni | 7.2 | 1.8 | 75 |
| | Zn | 0.7 | 0.1 | 86 |
| | Cd | 0.6 | 0.2 | 67 |
| | Pb | 5.7 | 2.1 | 63 |
| | Ag | 0.07 | 0.01 | 86 |
| 7 | Fe | 17.3 | 4.2 | 76 |
| | Cu | 10.4 | 6.3 | 40 |
| | Ni | 7.7 | 3.3 | 64 |
| | Zn | 0.7 | 0.2 | 72 |
| | Cd | 0.9 | 0.4 | 56 |
| | Pb | 3.4 | 1.9 | 45 |
| | Ag | 0.05 | 0.01 | 80 |

We claim:

1. A process for preparing a biosorbent for heavy metals having polyaminosaccharide sodium phosphate as the main ingredient, said biosorbent being prepared from a microbial biomass of *Aspergillus, Penicillium, Trichoderma,* or *Micrococcus genus*, comprising the steps of:

I) hydrolyzing the biomass with 0.5 to about 5.0% phosphoric acid solution;

ii) removing lipid soluble material from the product of step (I) with butanol or n-hexane;

iii) reacting and treating the product of step (ii) with 1 to about 40% sodium hydroxide or sodium bicarbonate solution;

iv) removing soluble materials from the product of step (iii) with a lower alcohol; and v) filtering and drying the product of step (iv) to obtain the biosorbent.

2. The process according to claim 1, wherein the microorganism used for the microbial biomass is *Aspergillus niger, Penicillium chrysogenum, Trichoderma reesei,* or *Micrococcus luteus*.

3. The process according to claim 1, wherein the soluble materials are removed in step (iv) with a lower alcohol selected from the group consisting of methanol, ethanol, isopropanol, and combinations thereof.

4. The biosorbent produced by the process of claim 1, wherein the number average molecular weight of the biosorbent is 50,000 to about 200,000, and 1 gram of dried biosorbent contains 200 to about 400 mg of glucosamine, 70 to about 200 mg of amino acid, 30 to about 50 mg of organic phosphorus compounds and other residual compounds.

5. The biosorbent according to claim 4, wherein the IR spectrum of the biosorbent shows the absorption wavelengths ($cm^{-1}$) at 3000 to about 3500, 2300, 1650, 1550, 1470, 1380, 1320 to about 1340, 1160, 1050, 900, 780, and 600.

* * * * *